(12) United States Patent
Popescu et al.

(10) Patent No.: US 11,209,513 B2
(45) Date of Patent: Dec. 28, 2021

(54) METHOD AND SYSTEM FOR COMPENSATING STRAY MAGNETIC FIELDS IN A MAGNETIC RESONANCE IMAGING SYSTEM

(71) Applicant: Siemens Healthcare GmbH, Erlangen (DE)

(72) Inventors: Stefan Popescu, Erlangen (DE); Markus Vester, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/101,292

(22) Filed: Nov. 23, 2020

(65) Prior Publication Data
US 2021/0156941 A1    May 27, 2021

(30) Foreign Application Priority Data
Nov. 27, 2019 (EP) .................................... 19211915

(51) Int. Cl.
| G01R 33/54  | (2006.01) |
| G01R 33/56  | (2006.01) |
| G01R 33/565 | (2006.01) |

(52) U.S. Cl.
CPC ....... *G01R 33/543* (2013.01); *G01R 33/5608* (2013.01); *G01R 33/56572* (2013.01)

(58) Field of Classification Search
USPC ......................................................... 324/309
See application file for complete search history.

(56) References Cited

U.S. PATENT DOCUMENTS

| 4,864,240 A | 9/1989 | Young |
| 2002/0030491 A1 | 3/2002 | Kose |

(Continued)

FOREIGN PATENT DOCUMENTS

| EP | 0311294 A2 | 4/1989 |
| EP | 3736590 A1 | 11/2020 |

(Continued)

OTHER PUBLICATIONS

Matsuda Y et al.: "Super-Parallel MR Microscope"; Magnetic Resonance in Medicine; John Wiley & Sons, Inc; US; vol. 50; Jan. 1, 2003; pp. 183-189; XP002458782; ISSN: 0740-3194; DOI: 10.1002/MRM.10515; 2003.

(Continued)

*Primary Examiner* — Rodney E Fuller
(74) *Attorney, Agent, or Firm* — Schiff Hardin LLP

(57) ABSTRACT

In a method for compensating stray magnetic fields in a magnetic resonance imaging system with two or more examination areas: a value for a predefined first magnetic field to be applied in a first examination area, in addition to a basic magnetic field is provided; information defining a predefined sequence control pulse to be applied in a second examination area is provided; a stray magnetic field in the second examination area resulting from application of the first magnetic field in the first examination area is determined; a compensated sequence control pulse for the second examination area is calculated from the predefined sequence control pulse and the determined stray magnetic field; and the compensated sequence control pulse is applied to the second examination area.

16 Claims, 4 Drawing Sheets

(56) References Cited

U.S. PATENT DOCUMENTS

| | | |
|---|---|---|
| 2015/0084631 A1 | 3/2015 | Bradshaw |
| 2020/0116807 A1* | 4/2020 | Holscher .............. G01R 33/446 |
| 2020/0355764 A1 | 11/2020 | Popescu |
| 2020/0355771 A1 | 11/2020 | Popescu et al. |
| 2021/0156936 A1* | 5/2021 | Popescu ........... G01R 33/34084 |
| 2021/0156937 A1* | 5/2021 | Popescu ............. G01R 33/4816 |

FOREIGN PATENT DOCUMENTS

| | | |
|---|---|---|
| EP | 3736591 A1 | 11/2020 |
| JP | H10234704 A | 9/1998 |

OTHER PUBLICATIONS

European Search Report dated Jun. 3, 2020, Application No. 19211915.4.

\* cited by examiner

METHOD AND SYSTEM FOR COMPENSATING STRAY MAGNETIC FIELDS IN A MAGNETIC RESONANCE IMAGING SYSTEM

CROSS REFERENCE TO RELATED APPLICATIONS

This patent application claims priority to European Patent Application No. 19211915.4, filed Nov. 27, 2019, which is incorporated herein by reference in its entirety.

BACKGROUND

Field

The disclosure describes a method and a system for compensating stray magnetic fields in a magnetic resonance imaging system ("MRI-system") with two or more examination areas, and such MRI-System.

Related Art

For more than four decades, the principle of magnetic resonance imaging ("MRI") has been used for imaging and other measurements. Despite this long time and the importance of this method of measurement, only two magnet designs are currently used for clinically used MRI systems or MRI scanners: C magnet forms and solenoids. Operation of this type of MRI scanner still are problematic for the clinical workflow.

The most serious problems occur with regard to the extensive stray magnetic fields around these scanners. In order to cope with this problem and avoid accidents and damage, the hospital administration must delineate a strictly controlled area within and in the vicinity of the MRI examination rooms by limiting the access of people and equipment. Damage can occur if metallic or magnetic parts are attracted by the strong magnets of the MRI scanner and accelerated in the direction of the scanner volume.

Another problem is that the MRI scanners, which use a solenoid-magnet design, "enclose" patients in a narrow patient tunnel, which in particular can cause claustrophobia. This claustrophobia may be so strong in some patients that no MRI scan can be performed. Moreover, due to the narrowness of the examination tunnel, the access of the medical staff to the patient is severely restricted, which is unfavorable for interventional or therapeutic procedures, in particular with regard to real-time MRI imaging.

Typically, MRI scanners use a self-shielded, solenoid-type superconducting magnet to reduce the strength of the leakage magnetic field resulting from the coil of the basic field magnet. An actively shielded basic field magnet is much more expensive than an unshielded one. In addition, the shield coils reduce the efficiency of the basic magnetic field that can be used for measurements in an examination tunnel. Active shielded magnets have a larger diameter (about 220 cm) than unshielded magnets (about 145 cm).

Alternative designs for MR scanners use a C-shaped magnet. This can be either a permanent magnet or an electromagnet consisting of two Helmholtz coils. The C-shaped magnets have two magnetic pole pieces which create a vertical basic magnetic field in their space. An analogous structure is a portal magnet, which is mechanically more robust, and in some embodiments can also be realized with superconducting Helmholtz coils. The C-shape and the portal magnets have the advantage of open access to the patient and additionally reduce claustrophobic feelings. However, such a structure requires a very robust mechanical construction to counteract the enormous magnetic attraction between the two opposed basic field magnets. To reduce the spread of stray magnetic fields, these magnet architectures typically use an iron yoke to guide the magnetic field lines outside the imaging volume. The iron yoke is one of the most cost-effective shields. The disadvantage of such a yoke is the big size, weight and volume of the MR scanner.

One approach to solve these problems has been introduced a short time ago. This approach is based on an MRI system with a toroidal magnetic field. Unlike the prior art of MR magnets that use solenoid or Helmholtz-pair magnet coils, the toroid coils tend to confine the magnetic field inside the torus with only a small and not so far reaching stray magnetic field. This system not only overcomes the problems of stray magnetic field and a light construction, it also offers the opportunity to realize two or more examination areas in one single MRI-system. An example for such MRI-system is a basic field magnet arrangement with three, four, six or eight (e.g. identical) basic field magnet segments arranged in a star shape about a central axis with a rotational symmetry (e.g. 60° for six magnets and six examination areas). The basic magnetic field has a main direction which runs in the form of a toroidal magnetic field.

There are local gradient systems with coil pairs arranged parallel left and right of a patient. However, although such known gradient systems can also be used for these new MRI-systems, there is currently no gradient system working in an optimal way together with these MRI-systems.

In a MRI-system with more than one examination area, with a gradient system installed in an examination area, there appear stray gradient fields in the other examination areas. In the case, each examination area comprises a gradient system, there are stray gradient fields all over the examination areas. These stray gradient fields affect the examinations negatively. Thus, stray gradient fields in adjacent regions would need to be very well shielded, because otherwise even small asynchronous perturbations, even in the order of about 1 ppm, could already produce image artefacts.

Typical actively shielded gradient coils reduce stray fields only by one order of one magnitude. This is enough to reduce the amplitude of the eddy currents induced into electrically conductive parts of the magnet, but not sufficient for effectively shielding magnetic stray fields in adjacent examination areas. Simultaneous but asynchronous imaging in MRI systems with two or more examination areas needs shielding between individual gradient systems which is several orders of magnitude better than the prior art.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
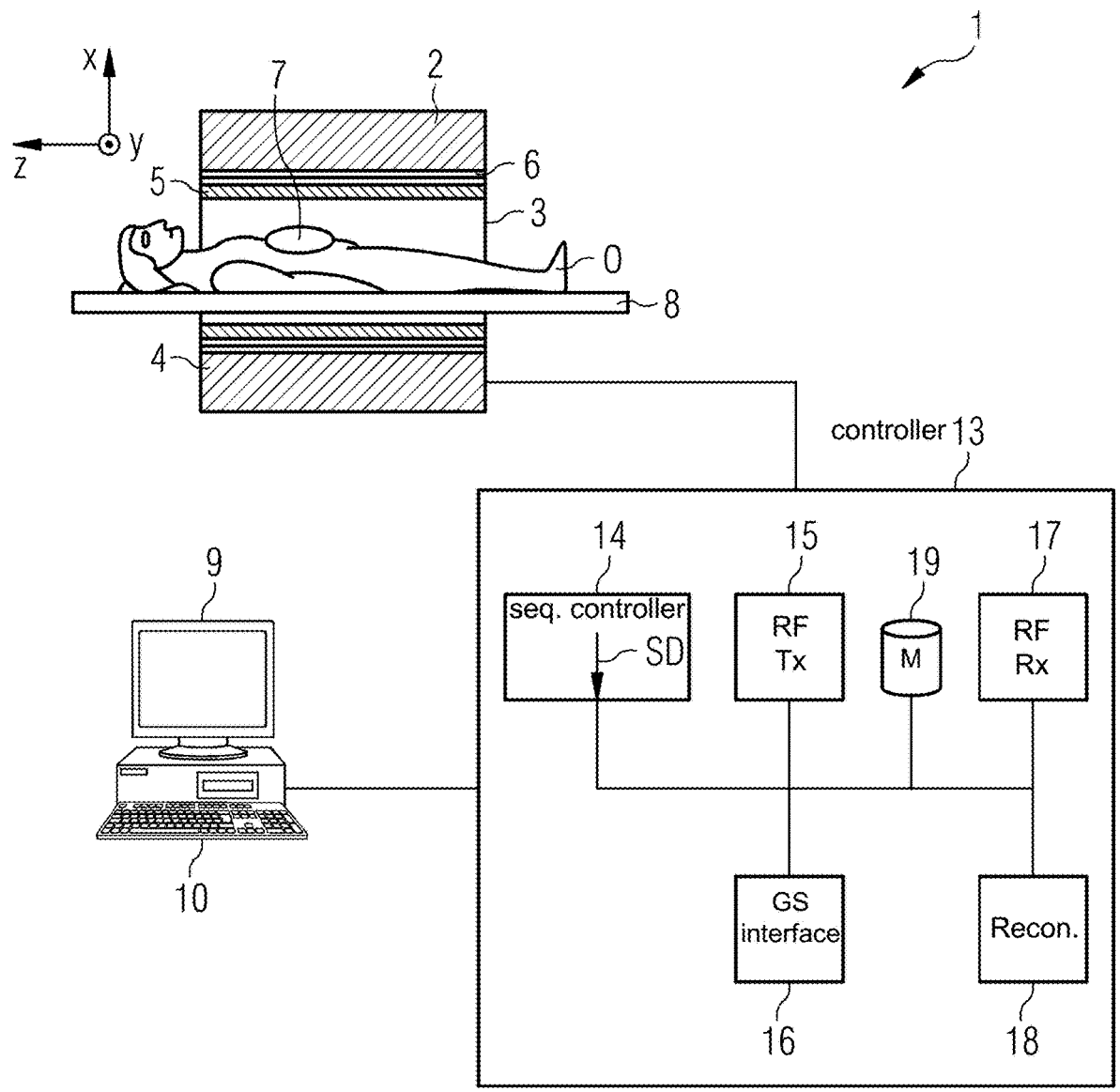
FIG. 1 shows a magnetic resonance imaging (MRI) system according to an exemplary embodiment of the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

It is the object of the present disclosure to improve known MRI-systems with more than one examination area to facilitate improved measurements by compensating stray gradient fields.

The method according to the disclosure for compensating stray magnetic fields in a magnetic resonance imaging system with two or more examination areas comprises the following steps:
  providing a value for a predefined first magnetic field to be applied in a first examination area, in addition to a basic magnetic field,
  providing a predefined sequence control pulse to be applied in a second examination area (especially adjacent to the first examination area, since the effect is strongest in adjacent areas),
  determining a stray magnetic field in the second examination area in the case the first magnetic field is applied in the first examination area,
  calculating a compensated sequence control pulse for the second examination area from the predefined sequence control pulse and the determined stray magnetic field, wherein the compensated sequence control pulse is calculated such that a measurement in the second examination area can be performed despite the stray field,
  applying the compensated sequence control pulse to the second examination area and
  repeating these steps for a further examination area, especially for all examination areas.

The first magnetic field is not the basic magnetic field, since it should be applied in addition to the basic magnetic field. In an exemplary embodiment, it is a gradient field, but could also be another magnetic field, e.g. a shim field or a field of an active shielding apparatus. The value for this first magnetic field that is used to be applied in the first examination area is well known. When applied in the first examination area, this first magnetic field produces stray fields in the other examination area(s).

The stray fields affect measurements in a second examination area. If the second examination area is adjacent the first examination area (wherein this case is preferred, since the stray field is strongest in adjacent areas), the disturbance of a measurement by the stray magnetic field is grave. For a measurement, a predefined sequence control pulse is applied in the second examination area, wherein this predefined sequence control pulse is preferably a predefined second magnetic field (in particular a gradient field), or a predefined RF-signal. Since the stray field affects a measurement with this sequence control pulse, this sequence control pulse is adjusted to the stray field with the following steps.

The information defining a predefined sequence control pulse are data about the strength and the direction of the sequence control pulse. Since in an MRI system there are defined magnet coils and RF-coils/antennae, the data may comprise information about a signal-amplitude or a current and the coil or antenna where this signal is to be applied.

It should be noted that in all examination areas of the MRI system the influences of stray magnetic fields should be compensated. Thus, preferably values for predefined sequence control pulses of all examination areas should be provided and the method should be performed on all examination areas while regarding any examination area as first area and any other examination area as second examination area.

Before, during or after providing any information about a predefined sequence control pulse, there is determined the stray magnetic field in the second examination area, e.g. its direction and its strength (magnetic field vector). This is the stray magnetic field of the first magnetic field. This step can be achieved by calculating or by measuring the stray magnetic field.

For example, the first magnetic field could be applied in the first examination area and the stray magnetic field can be measured in the second examination area (e.g. for different currents inducing the first magnetic field). The measured values can be stored and used for the determination of the stray magnetic field in the second examination area for the case that the first magnetic field is applied in the first examination area (with a predefined current). However, if the properties of the MRI-scanner are well known, the magnetic field can also be calculated (e.g. in a simulation). Last, for a group of identical MRI-scanners, a set of stored values can be used for the determination.

Using the determined stray magnetic field, and the provided (predefined) sequence control pulse, a compensated sequence control pulse can be calculated for the second examination area. This compensated sequence control pulse can be determined directly, or a correction term can be calculated and added to/subtracted from the predefined sequence control pulse. Since the direction of the predefined sequence control pulse and the stray field may be important, it is preferred to calculate a resulting compensated vector from a vector representing the predefined sequence control pulse and a correction vector (based on the stray field).

After that, the compensated sequence control pulse is applied to the second examination area. This application is well known and the compensated sequence control pulse is applied instead of the predefined sequence control pulse.

This inventive solution allows an active compensation of the stray gradient fields at least in the first order. With his compensation it is possible to simultaneously and independently acquire images in different examination areas, wherein in each examination area there may operate a dedicated three-axis gradient system. A compensation of stray fields up to the first order is good enough if the target field of view is not too large and the active shielding of the gradient coils is reasonably effective. Nevertheless, this method can be extended to correct for higher order stray fields. This would preferably require a set of dynamic higher-order shim coils and associated coil current amplifiers, and correspondingly a larger sensitivity matrix to invert. The higher order compensation is explained further below.

Although the disclosure is very advantageous for star-shaped magnet arrangements, it is also advantageous for other MRT-systems with e.g. a linear arrangement of examination areas or an arrangement of "satellite examination areas" using the basic magnetic field of a central examination area.

A system according to the disclosure for compensating stray magnetic fields in a magnetic resonance imaging system with two or more examination areas is especially designed to perform a method according to the disclosure. The system comprises the following components:

- A data interface for receiving a value for a predefined first magnetic field to be applied in a first examination area, in addition to a basic magnetic field, and information defining a predefined sequence control pulse to be applied in a second examination area. Such data interface is well known and is preferably designed to read a data memory or communicate via a data-network.
- A determination unit (determiner) designed to determine a stray magnetic field in the second examination area for the case that the first magnetic field is applied in the first examination area. This determination unit may be designed to calculate the stray magnetic field from information about the respective MRI-scanner. However, it may also comprise a sensor unit to measure a stray magnetic field in the respective examination area. The determination unit may also be designated "stray field determination unit".
- A calculator designed to calculate a compensated sequence control pulse for the second examination area from the predefined sequence control pulse and the determined stray magnetic field. The calculator may also be designated "compensation unit".
- An applicator designed to apply the compensated sequence control pulse to the second examination area. This applicator may be a data interface sending the data of the compensated sequence control pulse to a controller of a MRI scanner. However, it may also comprise units that are able to directly drive coils or antennae of the MRI-system (i.e. applying currents to these coils).

A controller according to the disclosure for controlling a magnetic resonance imaging system comprises a system according to the disclosure. Alternatively or additionally it is designed to perform the method according to the disclosure. The controller may comprise additional units or devices for controlling components of a magnetic resonance imaging system, e.g. a sequence controller for measurement sequence control, a memory, a radio-frequency transmitter that generates, amplifies and transmits RF pulses, a gradient system interface, a radio-frequency receiver to acquire magnetic resonance signals and/or a reconstructor to reconstruct magnetic resonance image data.

A magnetic resonance imaging system comprises two or more examination areas and a controller according to the disclosure. A MRI-scanner according to an exemplary embodiment of such magnetic resonance imaging system includes an inclined arrangement of basic field magnets, e.g. a star-shaped arrangement. MRI scanners with a toroidal MRI scanner architecture are used in one or more aspects.

Some units or modules of the system or the controller mentioned above can be completely or partially realized as software modules running on a processor of a system or a controller. A realization largely in the form of software modules can have the advantage that applications already installed on an existing system can be updated, with relatively little effort, to install and run these units of the present application. The object of the disclosure is also achieved by a computer program product with a computer program that is directly loadable into the memory of a device of a system or a controller of a magnetic resonance imaging system, and which comprises program units to perform the steps of the inventive method when the program is executed by the controller or the system. In addition to the computer program, such a computer program product can also comprise further parts such as documentation and/or additional components, also hardware components such as a hardware key (dongle etc.) to facilitate access to the software. It should be noted that an application of a sequence control pulse is at first hand the action "sending respective data about the amplitude of the pulse to an amplifier unit". That can be performed by a computing unit with a data interface.

A computer readable medium such as a memory stick, a hard-disk or other transportable or permanently-installed carrier can serve to transport and/or to store the executable parts of the computer program product so that these can be read from a processor unit of a controller or a system. A processor unit can comprise one or more microprocessors or their equivalents.

A method is applicable when the sequence control pulse is a second magnetic field. This method comprises the following steps:

- In addition to the value for the predefined first magnetic field, providing a value for a predefined second magnetic field (i.e. the sequence control pulse) to be applied in a second examination area, (especially adjacent to the first examination area). In an exemplary embodiment, the first and second magnetic fields are both gradient fields. However, for compensating shifts for the RF-readout, the second magnetic field may also be the B0 field that is affected by the first magnetic field (e.g. a gradient field).
- Then, the stray magnetic field of the first magnetic field in the second examination area is determined as described above.
- After determining the stray magnetic field in the second examination area, calculating a compensated magnetic field for the second examination area from the predefined second magnetic field and the determined stray magnetic field. This is especially achieved by adding or subtracting the vector of the stray magnetic field to/from the vector of the first magnetic field. However, also a correction field can be calculated and added to/subtracted from (depending on the directions) the second magnetic field. Technically, in an exemplary embodiment, a compensated current is calculated that has to be applied instead of a predefined current (of the predefined second magnetic field) in a predefined coil.
- Applying the compensated magnetic field to the second examination area. In an exemplary embodiment, this is performed for all gradients Gx, Gy and Gz, in each examination area. Technically, in an exemplary embodiment, this is achieved by applying the above mentioned compensated current to the predefined coil. It should be noted that since the current produces the magnetic field and is directly defining the field, "current" can be read instead of "magnetic field".

A method is applicable when the sequence control pulse is an RF-signal. This method may be applied alternatively or additionally to the method for magnetic fields described before. It should be noted that stray fields leaking into an examination area shift the effective basic magnetic field B0 by a fraction ΔB0 and, therefore, also the Larmor frequency by an offset Δf0.

In an exemplary embodiment, the method comprises the following steps:
  In addition to the value for the predefined first magnetic field, providing a value for the frequency (f0) of a predefined RF-signal (i.e. here the sequence control pulse) to be applied in a second examination area (especially adjacent to the first examination area).
  After determining the stray magnetic field in the second examination area, calculating a compensated RF-signal for the second examination area from the predefined RF-signal and the determined stray magnetic field. This is especially achieved by calculating a compensation frequency (Δf0), i.e. the shift of the Larmor frequency in the second examination area due to the influence of the stray magnetic field, and calculating the compensated frequency from the predefined frequency f0 and the compensation frequency Δf0.
  Applying the compensated RF-signal to the second examination area. This is especially performed by incorporating the leakage from all other gradient coils into a first correction of the Larmor frequency by an offset Δf0 corresponding to an average shift in the static magnetic field ΔB0. In an exemplary embodiment, the frequency correction is implemented by digitally adjusting the frequency offset of the clock synthesizer for each examination region.

In a method according to an exemplary embodiment, a field shift-matrix with the coefficients $k_{m,n}$ is calculated for a magnetic resonance system with a number of M examination areas and a gradient system for L axes in each examination area. Usually L equals 3 for an X-, an Y- and a Z-axis. This field shift-matrix can be measured or provided (calculated or read from a data memory). Regarding the indices, m runs from 1 to M and represents the examination area and n runs from 1 to L×M and represents the gradient axes in the different examination areas. For example, n=1 means the X-gradient axis in the first examination area, n=2 the Y-gradient axis in the first examination area, n=3 the Z-gradient axis in the first examination area, n=4 the X-gradient axis in the second examination area and so on.

The calculation of the $k_{m,n}$ is done from a function of a time-dependent field change $\Delta B0_m$ within the isocenter of each examination region m based on the formula $k_{m,n}=g(\Delta B0_m)_n$, wherein g( ) is a function depending linearly from $\Delta B0_m$. Preferably, the field shift coefficients $k_{m,n}$ are precalculated by using data from the gradient coil design, or they are obtained from calibration tests.

The compensated sequence control pulse for an examination area m is then calculated on the basis of the field-shift matrix, i.e. from the coefficients $k_{m,n}$. In an exemplary embodiment, the compensation frequency $\Delta f0_m$ for compensating an RF-signal for an examination area m is calculated based on the field-shift matrix based on the formula $$\Delta f0_m = \gamma \sum_{n=1}^{N} g(k_{m,n}), \quad (1)$$

wherein γ is the gyromagnetic constant and $g(k_{m,n})$ is a function of $k_{m,n}$ resulting in a magnetic flux density.

Preferably, the coefficients $k_{m,n}$ of the field shift-matrix are calculated with $k_{m,n}=\Delta B0_m/I_n$, depending from an electric current $I_n$ in a gradient coil $C_n$ of the gradient system (i.e. $g(k_{m,n})=\Delta B0_m/I_n$). Accordingly, the compensation frequency $\Delta f0_m$ for compensating an RF-signal for an examination area m is calculated from the currents $I_n$ in the magnet coils of the examination areas and the field-shift matrix based on the formula $$\Delta f0_m = \gamma \sum_{n=1}^{N} (k_{m,n} I_n). \quad (2)$$

For example, for the B0 correction the time-dependent field changes within the isocenter of the examination region m can be calculated by adding up all stray field contributions of the gradient coils (known by the currents In in all other active gradient coils or measured). Typically, there will be three field shift coefficients from each other examination area, requiring a summation over 18 terms for a scanner having six examination regions. It should be noted that some of the $k_{m,n}$ terms may be zero (i.e. the self-terms $k_{m,n}$), but also some cross-terms may be near zero by symmetry. For example, any Gy gradient coil should barely produce a B0 shift into any other examination region.

In a method according to an exemplary embodiment, the sequence control pulse is a gradient-signal and a sensitivity matrix S is created comprising the contributions of each gradient field to each examination area. A compensated gradient field for a gradient axis in an examination area is calculated based on that sensitivity matrix S.

In an exemplary embodiment, where P gradient coils are present, the matrix S comprises P×P coefficients $s_{p,n}$ with both p and n running from 1 to P, wherein especially P=L×M for a number of M examination areas and a gradient system for L axes (preferably 3) in each examination area. It should be noted that each gradient system should have its own local coordinate system adjusted to the respective examination area.

Preferably, the coefficients $s_{p,n}$ of the sensitivity matrix S correspond to gradient fields taking effect relative to the (local) axes of the gradient system in the individual examination areas and are calculated, measured or provided.

In an exemplary embodiment, a row or column of the sensitivity matrix S comprises values for a magnetic gradient field applied in the axes of the gradient system in the individual examination areas in the case a current $I_n$ flows through one gradient coil $C_n$, (i.e. the predefined gradient coil for the current $I_n$). In an exemplary embodiment, the coefficients $s_{p,n}$ correspond to a gradient field-value $G_p$ divided by a current $I_n$ through a gradient coil $C_n$. Here it should be noted that every current only runs through one clearly defined coil (every current through another coil). The current for the Z-gradient in examination area 1 should run through the coil for the z-gradient in this examination area 1 and so on. However, a current running through a coil induces a magnetic field in the respective examination area (i.e. $s_{n,n}$) and a stray field in the other examination areas (i.e.

$s_{p,n}$ with p≠n), wherein the stray field is strongest in adjacent examination areas. Thus, in any column and row of the matrix S, there should be one maximum coefficient with adjacent coefficients representing stray fields. The other coefficients are typically zero or near zero.

In an exemplary embodiment, for a predefined gradient value $G_n$ of a gradient coil $C_n$ of the gradient system, a current $I_n$ to be applied to the gradient coil $C_n$ is calculated from the sensitivity matrix S. In an exemplary embodiment, this is done by using a predefined gradient vector G comprising predefined gradient values $G_p$ for the axes of the gradient system in the individual examination areas. Then a vector I comprising the (compensated) currents $I_n$ to be applied to the gradient coils $C_n$ is calculated from the inverted sensitivity matrix $S^{-1}$ based on the formula I=$S^{-1}$·G. Thus, the vector G filled with the predefined values for the gradients is corrected by the sensitivity matrix S and the resulting vector I comprises the currents that have to be applied to obtain the correct gradient fields despite stray fields. In an exemplary embodiment, both the gradient and the currents waveforms are functions of time.

For example, there is a gradient sensitivity matrix S $\{s_{p,n}=G_p/I_n,$ with p,n=1 . . . 3×M$\}$ (for M examination areas each having three gradient axes), which describes the spatial derivative of the stray field around the isocenter in all three directions of the local coordinate system, caused by the (initial) gradient current $I_n$. In this example, S is an 18×18 matrix for 6 examination areas, which practically contains some zero or near-zero terms far from the diagonal. Now corrections on the m-th gradient current should be applied to cancel the unwanted contribution from all other gradient currents, which will again change the stray fields in all other examination regions. Normally the correction would need to be calculated iteratively. A straightforward yet non-iterative solution is to invert the gradient sensitivity matrix after a calibration (see above). Then in order to realize the target gradient waveforms for 6×3 gradients, the required waveforms vector of 18 gradient currents is simply calculated by above formula I=$S^{-1}$·G, with G being the matrix of the 18 target gradients to be realized within the examination regions.

In a method according to an exemplary embodiment, the compensated sequence control pulse is calculated iteratively by calculating a compensated first magnetic field in the first examination area on the basis of the stray magnetic field of the compensated sequence control pulse in the first examination area. If there are applied corrections on the m-th gradient current to cancel the unwanted contribution from all other gradient currents, this will again change the stray fields in all other examination regions. Thus, in an exemplary embodiment, a correction is added that is calculated iteratively.

In an exemplary embodiment, a system is designed to calculate and apply a compensated sequence control pulse in form of a gradient field and/or a RF-signal.

FIG. 1 shows a schematic representation of a magnetic resonance imaging system 1 ("MRI-system"). The MRI system 1 includes the actual magnetic resonance scanner (data acquisition unit) 2 with an examination space 3 or patient tunnel in which a patient or test person is positioned on a driven bed 8, in whose body the actual examination object O is located.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI system 1 shown here is a whole-body system with a patient tunnel into which a patient can be completely introduced. However, in principle the disclosure can also be used at other MRI systems, for example with a laterally open, C-shaped housing, as well as in smaller magnetic resonance scanners in which only one body part can be positioned.

Furthermore, the MRI system 1 has a central controller 13 that is used to control the MRI system 1. This central controller 13 includes a sequence controller 14 for measurement sequence control. With this sequence controller 14, the series of radio-frequency pulses (RF pulses) and gradient pulses can be controlled depending on a selected pulse sequence. In an exemplary embodiment, the controller 13 includes processor circuitry that is configured to perform one or more functions and/or operations of the controller 13, including controlling the MRI system 1.

To output the individual RF pulses of a pulse sequence, the central controller 13 has a radio-frequency transmitter 15 that generates and amplifies the RF pulses and feeds them into the RF transmission antenna system 5 via a suitable interface (not shown in detail). To control the gradient coils of the gradient system 6, the controller 13 has a gradient system interface 16. The sequence controller 14 communicates in a suitable manner with the radio-frequency transmitter 15 and the gradient system interface 16 to emit the pulse sequence.

Moreover, the controller 13 has a radio-frequency receiver 17 (likewise communicating with the sequence controller 14 in a suitable manner) in order to acquire magnetic resonance signals (i.e. raw data) for the individual measurements, which magnetic resonance signals are received in a coordinated manner from the RF reception antenna system 7 within the scope of the pulse sequence.

A reconstructor 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central controller 13 can take place via a terminal 10 with an input unit and a display unit 9, via which the entire MRI system 1 can thus also be operated by an operator. MR images can also be displayed at the display unit 9, and measurements can be planned and started by means of the input unit (possibly in combination with the display unit 9), and in particular suitable control protocols can be selected (and possibly modified) with suitable series of pulse sequence PS as explained above.

The MRI system 1 according to the disclosure, and in particular the controller 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 2:
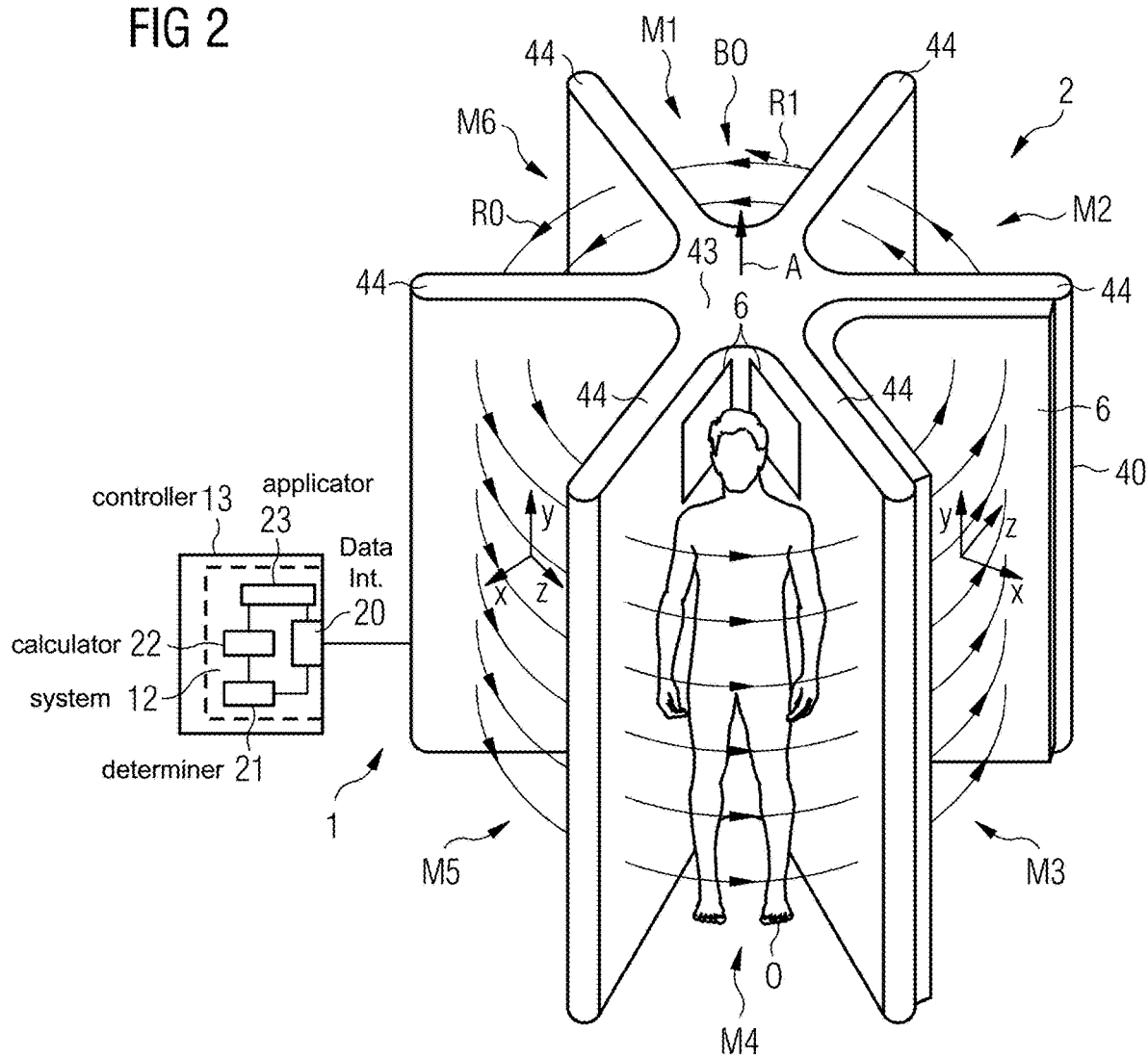
FIG. 2 shows a magnetic resonance tomography system with a star-shaped basic field magnet arrangement according to an exemplary embodiment of the disclosure.

FIG. 2 shows an exemplary embodiment of a magnetic resonance tomography system 1 with a star-shaped basic field magnet arrangement 40.

Shown here is a magnetic resonance scanner 2, the function of which can be controlled by a controller 13. The controller 13 can in principle be constructed in a similar manner and have the same components as the controller 13 in a conventional MR system according to FIG. 1. Likewise, it can also have a suitable terminal or the like (which is not shown here).

Figure 4:
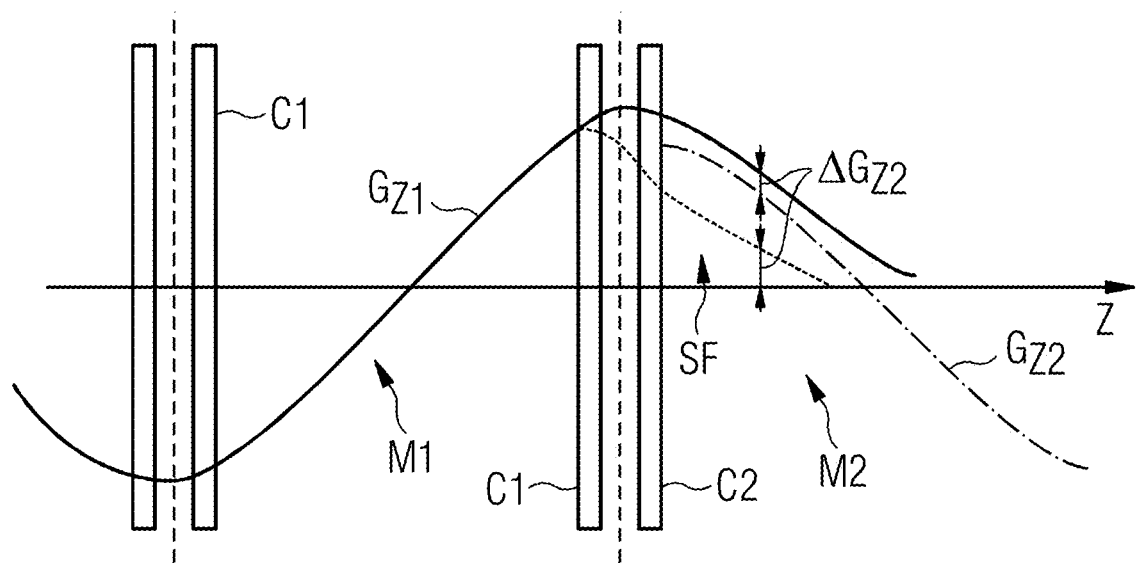
FIG. 4 shows an example of a stray field distribution according to an exemplary embodiment of the disclosure.

In an exemplary embodiment, the controller 13 comprises a system 12 for compensating stray magnetic fields in a magnetic resonance imaging system with two or more examination areas according to the disclosure. Regarding pulses and fields, this is shown in FIG. 4 and explained in the following. In an exemplary embodiment, the system 12 (compensation system) comprises:

A data interface 20 for receiving a value for a predefined first magnetic field to be applied in a first examination area M1, M2, M3, M4, M5, M6 (each examination area may serve as first examination area), in addition to a basic magnetic field B0, and information defining a predefined sequence control pulse to be applied in a second examination area M1, M2, M3, M4, M5, M6 (any other examination area than the first examination area may serve as second examination area).

A determination unit (determiner) 21 designed to determine a stray magnetic field SF in the second examination area M1, M2, M3, M4, M5, M6 for the case that the first magnetic field is applied in the first examination area M1, M2, M3, M4, M5, M6.

A calculator 22 designed to calculate a compensated sequence control pulse for the second examination area M1, M2, M3, M4, M5, M6 from the predefined sequence control pulse and the determined stray magnetic field SF.

An applicator 23 designed to apply the compensated sequence control pulse to the second examination area M1, M2, M3, M4, M5, M6.

The basic field magnet arrangement 40 of the magnetic resonance scanner 2 in this figure comprises six (here identical) basic field magnet segments 44, which in this embodiment are arranged in a star shape about a central axis A with a rotational symmetry of 60°. The basic magnetic field B0 indicated by arrows has a basic field main direction R0, which runs in the form of a circle or a toroidal magnetic field.

Figure 3:
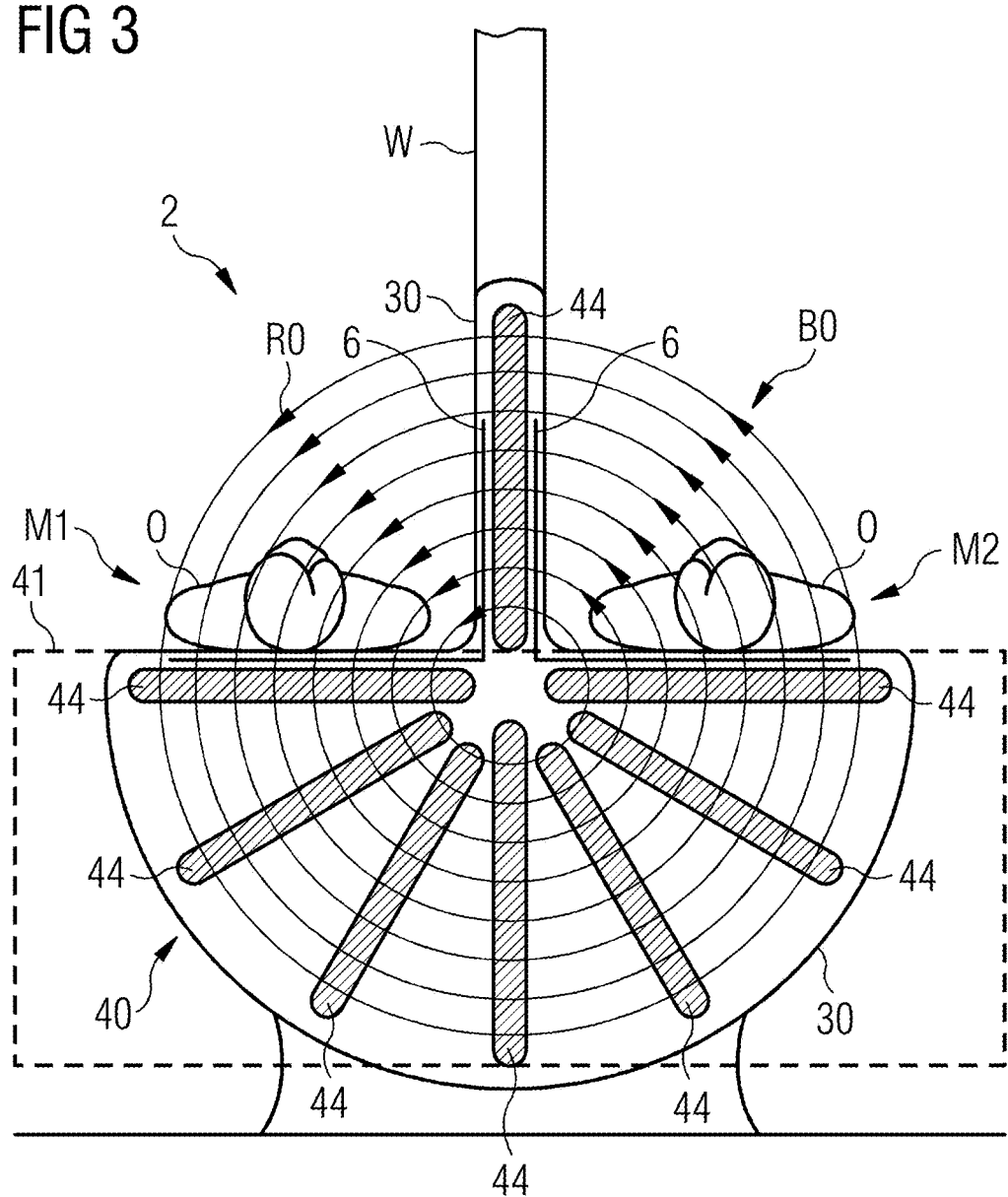
FIG. 3 shows a magnetic resonance scanner with two examination areas according to an exemplary embodiment of the disclosure.

In two examination areas there are shown local coordinate systems for the local gradient fields produced by gradient systems 6 (In FIG. 3 only two gradient systems 6 are shown in the examination area M4 at the front and the examination area M3 front right. Of course, all examination areas M1, M2, M3, M4, M5, M6 may comprise gradient systems). The y-axis points in this example always up, the z-axis follows the direction of the basic magnetic field B0 (at least in the isocenter) and the x-axis points perpendicular to the basic magnetic field B0 to the outside (at least from the isocenter). This scheme of local coordinate systems can be applied to all examination areas M1, M2, M3, M4, M5, M6, so that the x-axes and z-axes of the local coordinate systems are always different.

FIG. 3 shows a further exemplary embodiment of a magnetic resonance scanner 2 with two examination areas M1, M2. Here, only the lower half of the basic field magnet arrangement 40 is designed star-shaped as a group 41 of basic field magnet segments 44 and another basic field magnet segment 44 projects upwards and serves both for guiding the basic magnetic field B0 as well as part of a wall W between two examination area M1, M2, on which there are two patients as objects O to be examined. In the illustration it can be seen that the lower part of the wall W between the two patients is formed by the housing wall 30 of the magnetic resonance scanner 2, into which the basic field magnetic segment 44 is integrated between the examination area M1, M2. The wall W can serve not only as a privacy screen but also as an acoustic shield or RF shield.

The basic magnetic field B0 of this magnetic resonance scanner 2 becomes weaker toward the outside, which can be used for location coding, and is homogeneous in the longitudinal direction (orthogonal to the image plane). It is basically the same in shape in the two examination area M1, M2, with the only difference being that the course (in one direction through the surface on which the patient O is lying) is reversed. Again, the dimensions of the magnetic resonance scanner 2 can be chosen quite different.

The basic magnetic main field direction R0 is also circular here. A special feature of this embodiment is that the patients O are not in a narrow space, but can look freely to the ceiling. The inhomogeneity in the basic magnetic field B0, which is usually caused by the curvature, can be used, as mentioned, for spatial encoding resolution in one spatial direction, so that for total spatial resolution total spatial encoding only gradients have to be applied in the other spatial direction.

Due to its open design and the toroidal magnetic field, this arrangement allows easy and little restricted access to the patient. As a result of the special construction, magnetic forces are largely compensated as in FIG. 2 or diverted into areas which can be reinforced structurally well.

An example for a gradient system 6 is shown in both examination areas M1, M2. The V-shape of the gradient system 6 again follows the angle between two basic field magnets 44, i.e. here 90°.

FIG. 4 shows an example of a stray field SF distribution and magnetic fields. A stray gradient field produced by an activated Gz-gradient field $G_{Z1}$ leaks into an area. From left to the right, there runs the Z-axis of the local coordinate systems (see e.g. FIG. 2). In a star shaped arrangement of magnets, for example, the Z-axis of all coordinate systems runs in the shape of a circle or a polygon. This Z-axis is shown here in a straight line, where the examination areas M1, M2 are lying in a line adjacent to another. The dashed vertical lines should represent the borders of the examination areas M1, M2 (and also the basic field magnets). Shown as vertical boxes are coils C1, C2 for applying a Z-gradient in the examination areas M1, M2. In the first examination area M1 there is applied the Z-gradient field $G_{Z1}$ (i.e. the first magnetic field). The strength of the field is shown as distance from the Z-axis in the image plane (the x- and y-axes of the coordinate systems are not shown here).

As can be seen here, the first magnetic field (here the solid line) is not vanishing beyond the borders of the first examination area M1, but forming a stray field SF. Even if the primary gradient coil in region 1 is actively shielded (e.g. if the boxes also would act as magnet shields) then the stray fields are an order of magnitude smaller, however, a stray field SF would remain (dashed line spreading in the second examination area M2). A gradient field $G_{Z2}$ applied as second magnetic field in the second examination area M2 (dash-dotted line) would be affected by the stray fields SF due to field-interference.

To compensate the effects of stray magnetic fields SF, the disclosure determines the effect of the stray magnetic fields SF and amends the applied magnetic field (i.e. the compensated sequence control pulse) such that the resulting field is the second magnetic field despite the stray fiend SF. To achieve that, in an exemplary embodiment, the difference gradient field $\Delta G_{Z2}$ between the stray magnetic field SF and the predefined second magnetic field is calculated, as shown in the figure.

Regarding the solid line of the unshielded first magnetic field $G_{Z1}$, the stray field SF is bigger than the predefined second magnetic field $G_{Z2}$. Thus, a counteracting field has to be applied. The compensated sequence control pulse is here the difference gradient field $\Delta G_{Z2}$ applied against the predefined gradient field $G_{Z2}$. Regarding the dashed line of the shielded first magnetic field $G_{Z1}$, the stray field SF is smaller than the predefined second magnetic field $G_{Z2}$. Thus, a compensated field has to be applied that is weaker than the predefined second magnetic field $G_{Z2}$. The compensated sequence control pulse is here the predefined gradient field $G_{Z2}$ minus the difference gradient field $\Delta G_{Z2}$.

Figure 5:
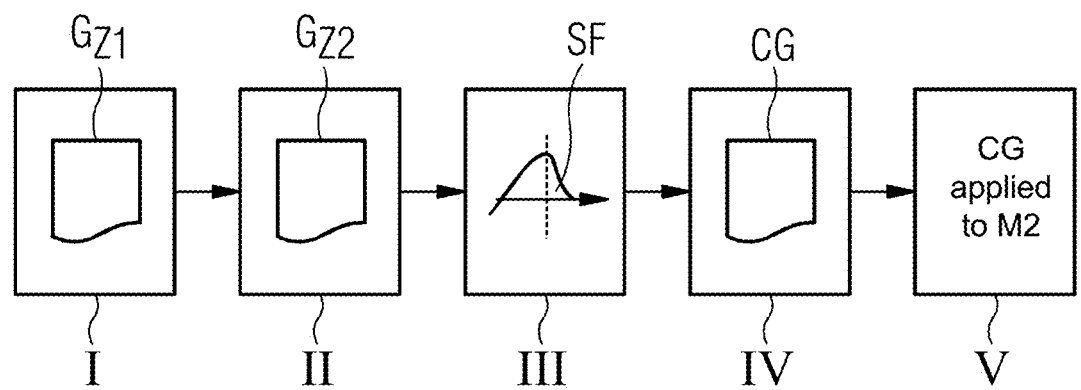
FIG. 5 shows a flowchart of a method according to an exemplary embodiment of the disclosure.

FIG. 5 shows a block diagram of the process flow of a method for compensating stray magnetic fields SF, according to an exemplary embodiment, in a magnetic resonance imaging system 1 (s. e.g. FIG. 2) with two or more examination areas M1, M2, M3, M4, M5, M6, according to the disclosure. For a visualization of the fields, see e.g. FIG. 4.

In step I, a value is provided for a predefined first magnetic field $G_{Z1}$ to be applied in a first examination area M1, in addition to a basic magnetic field B0.

In step II, information is provided defining a predefined sequence control pulse $G_{Z2}$ to be applied in a second examination area M2. In FIG. 4, this predefined sequence control pulse $G_{Z2}$ is a gradient field $G_{Z2}$, however, it could also be a RF-signal.

In step III, a stray magnetic field SF is determined in the second examination area M2 for the case that the first magnetic field $G_{Z1}$ is applied in the first examination area M1.

In step IV, a compensated sequence control pulse CG is calculated for the second examination area M2 from the predefined sequence control pulse $G_{Z2}$ and the determined stray magnetic field SF.

In step V, the compensated sequence control pulse CG is applied to the second examination area M2.

Although the present disclosure has been disclosed in the form of preferred embodiments and variations thereon, it will be understood that numerous additional modifications and variations could be made thereto without departing from the scope of the disclosure. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for compensating stray magnetic fields in a magnetic resonance imaging system with two or more examination areas, the method comprising:
   providing a value for a predefined first magnetic field to be applied in a first examination area, in addition to a basic magnetic field;
   providing information defining a predefined sequence control pulse to be applied in a second examination area;
   determining a stray magnetic field in the second examination area resulting from application of the first magnetic field in the first examination area;
   calculating a compensated sequence control pulse for the second examination area from the predefined sequence control pulse and the determined stray magnetic field; and
   applying the compensated sequence control pulse to the second examination area.

2. The method according to claim 1, wherein the sequence control pulse is a second magnetic field, the method comprising:
   in addition to the value for the predefined first magnetic field, providing a value for a predefined second magnetic field to be applied in the second examination area;
   after determining the stray magnetic field in the second examination area, calculating a compensated magnetic field for the second examination area from the predefined second magnetic field and the determined stray magnetic field; and
   applying the compensated magnetic field to the second examination area.

3. The method according to claim 2, wherein the sequence control pulse is a radio-frequency (RF) signal, the method comprising:
   in addition to the value for the predefined first magnetic field, providing a value for a frequency of a predefined RF signal to be applied in the second examination area;
   after determining the stray magnetic field in the second examination area, calculating a compensated RF signal for the second examination area from the predefined RF signal and the determined stray magnetic field; and
   applying the compensated RF signal to the second examination area.

4. The method according to claim 1, wherein the sequence control pulse is a radio-frequency (RF) signal, the method comprising:
   in addition to the value for the predefined first magnetic field, providing a value for a frequency of a predefined RF signal to be applied in the second examination area;
   after determining the stray magnetic field in the second examination area, calculating a compensated RF signal for the second examination area from the predefined RF signal and the determined stray magnetic field; and
   applying the compensated RF signal to the second examination area.

5. The method according to claim 1, wherein:
   for a magnetic resonance system with a number M of examination areas and a gradient system for L axes in each examination area, a field shift-matrix with the coefficients $k_{m,n}$ is calculated, measured or provided, where m=(1 ... M) and n=(1 ... L×M) from a function of a time-dependent field change $\Delta B0_m$, within an isocenter of each examination area of the M examination areas based on the formula $k_{m,n}=g(\Delta B0_m)_n$ and the compensated sequence control pulse for an examination area m of the M examination areas is calculated based on the field-shift matrix,
   the compensation frequency $\Delta f0_m$ for compensating an RF-signal for the examination area m is calculated based on the field-shift matrix according to:

$$\Delta f0_m = \gamma \sum_{n=1}^{N} g(k_{m,n}),$$

where γ is a gyromagnetic constant and $g(k_{m,n})$ is a function of $k_{m,n}$ resulting in a magnetic flux density.

6. The method according to claim 5, wherein:
   the coefficients $k_{m,n}$ of the field shift-matrix are calculated based on an electric current $I_n$ in a gradient coil $C_n$ of the gradient system according to $k_{m,n}=\Delta B0_m/I_n$, and
   the compensation frequency $\Delta f0_m$ for compensating an RF-signal for the examination area m is calculated based on the field-shift matrix according to:

$$\Delta f0_m = \gamma \sum_{n=1}^{N} (k_{m,n} I_n).$$

7. The method according to claim 1, wherein:
   the sequence control pulse is a gradient-signal and wherein a sensitivity matrix S is created comprising contributions of each gradient field to each examination area,
   a compensated gradient field for a gradient axis in an examination area is calculated based on the sensitivity matrix S, and
   for P gradient coils, the sensitivity matrix S comprises P×P coefficients $s_{p,n}$ with both p and n running from 1 to P, where P=L×M for a number of M examination areas and a gradient system for L axes in each of the M examination areas.

8. The method according to claim 7, wherein:
   coefficients $s_{p,n}$ of the sensitivity matrix S correspond to gradient fields taking effect relative to the axes of the gradient system in the individual examination areas of the M examination areas and are calculated, measured or provided, wherein a row or column of the sensitivity matrix S comprises values for a magnetic gradient field applied in the axes of the gradient system in the individual examination areas in the case a current $I_n$ flows thorough one gradient coil $C_n$, the coefficients $s_{p,n}$ correspond to a gradient field-value $G_p$ divided by a current $I_n$ through the gradient coil $C_n$.

9. The method according to claim 7, wherein:

for a predefined gradient value $G_n$ of a gradient coil $C_n$ of the gradient system, a current $I_n$ to be applied to the gradient coil $C_n$ is calculated from the sensitivity matrix S, and for a predefined gradient vector G comprising predefined gradient values $G_p$ for the axes of the gradient system in the individual examination areas of the M examination areas, a vector I comprising the currents $I_n$ to be applied to the gradient coils $C_n$ is calculated from the inverted sensitivity matrix $S^{-1}$ based on the formula I=S−1·G.

10. The method according to claim 1, wherein the compensated sequence control pulse is calculated iteratively by calculating a compensated first magnetic field in the first examination area based on the stray magnetic field in the first examination area of the compensated sequence control pulse in the second examination area.

11. A computer program which includes a program and is directly loadable into a memory of the magnetic resonance imaging system, when executed by a processor of the magnetic resonance imaging system, causes the processor to perform the method as claimed in claim 1.

12. A non-transitory computer-readable storage medium with an executable program stored thereon, that when executed, instructs a processor to perform the method of claim 1.

13. A system for compensating stray magnetic fields in a magnetic resonance imaging system with two or more examination areas, the system comprising:

a data interface configured to receive a value for a predefined first magnetic field to be applied in a first examination area, in addition to a basic magnetic field, and information defining a predefined sequence control pulse to be applied in a second examination area;

a determiner configured to determine a stray magnetic field in the second examination area resulting from application of the first magnetic field in the first examination area;

a calculator configured to calculate a compensated sequence control pulse for the second examination area based on the predefined sequence control pulse and the determined stray magnetic field; and an applicator configured to apply the compensated sequence control pulse to the second examination area.

14. The system according to claim 13, wherein the compensated sequence control pulse is a gradient field and/or a RF-signal.

15. A controller for controlling a magnetic resonance imaging system comprising the system according to claim 14.

16. A magnetic resonance imaging system comprising:

first and second examination areas; and a controller comprising:

a data interface configured to receive a value for a predefined first magnetic field to be applied in the first examination area, in addition to a basic magnetic field, and information defining a predefined sequence control pulse to be applied in the second examination area;

a determiner configured to determine a stray magnetic field in the second examination area resulting from application of the first magnetic field in the first examination area;

a calculator configured to calculate a compensated sequence control pulse for the second examination area based on the predefined sequence control pulse and the determined stray magnetic field; and an applicator configured to apply the compensated sequence control pulse to the second examination area.

* * * * *